US012678488B2

(12) United States Patent
Tian et al.

(10) Patent No.: US 12,678,488 B2
(45) Date of Patent: Jul. 14, 2026

(54) BATCH MANAGEMENT METHOD FOR IMPROVING FARROWING RATE OR NUMBER OF PIGLETS BORN ALIVE IN SWINE

(71) Applicant: CHINA AGRICULTURAL UNIVERSITY, Beijing (CN)

(72) Inventors: Jianhui Tian, Beijing City (CN); Shumin Wang, Beijing City (CN); Lei An, Beijing City (CN); Yue Wang, Beijing City (CN); Wei Zhao, Beijing City (CN); Linghua Cheng, Beijing City (CN); Jiage Dai, Beijing City (CN); Zhicheng Shi, Beijing City (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 16 days.

(21) Appl. No.: 18/797,749

(22) Filed: Aug. 8, 2024

(65) Prior Publication Data

US 2025/0332222 A1      Oct. 30, 2025

(30) Foreign Application Priority Data

Apr. 24, 2024    (CN) ......................... 202410498753.3

(51) Int. Cl.
| | |
|---|---|
| *A61K 38/24* | (2006.01) |
| *A61K 31/4196* | (2006.01) |
| *A61K 31/57* | (2006.01) |
| *A61K 31/575* | (2006.01) |
| *A61K 45/06* | (2006.01) |
| *A61P 15/08* | (2006.01) |

(52) U.S. Cl.
CPC .......... *A61K 38/24* (2013.01); *A61K 31/4196* (2013.01); *A61K 31/57* (2013.01); *A61K 31/575* (2013.01); *A61K 45/06* (2013.01); *A61P 15/08* (2018.01)

(58) Field of Classification Search
None
See application file for complete search history.

(56) References Cited

FOREIGN PATENT DOCUMENTS

CN        103169699      *    6/2013

OTHER PUBLICATIONS

Moles (The use of altrenogest in gilts, Oct. 7, 2023).*
Aly et al. Molecules, Jul. 2020;25(13)). (Year: 2020).*
Emami et al. (BMC Chem. Nov. 12, 2022; 16(1):91) (Year: 2022).*
First Office Action issued in Chinese Application No. 202410498753.3; mailed May 28, 2024; 10 pgs.
De Rensis, F., et al; "Control of estrus and ovulation: fertility to timed insemination of gilts and sows"; Theriogenology; 2016, 86(6), 24 pgs.
Li JJ, et al; "The technique and some existing problems of timing sperm transfusion in sows;" Swine Industry Science, 2018, 35(06): pp. 46-48.
Longenecker, D. E. , et al.; "Fertility Level of Sows Superovulated at Post-Weaning Estrus"; Missouri Agricultural Experiment Station Journal Series, No. 5265; 1968; 27:pp. 709-711.
Ling, Cheng, et al.; "Effects of simultaneous ovulation and timed fertilization program on reproductive performance of gilts"; Chinese Journal of Animal Husbandry, 2022, 58(08), pp. 235-242.

* cited by examiner

*Primary Examiner* — Tara L Martinez
(74) *Attorney, Agent, or Firm* — HAUPTMAN HAM, LLP

(57)          ABSTRACT
The disclosure relates to a batch management method for improving the farrowing rate or the number born alive in swine. It includes the following steps: synchronization of estrus in swine are used an exogenous gonadotropin(s) to synchronize follicular development, and then fed with 1-[bis (4-cyanophenyl)alkyl]-1,2,4-triazole after 6-12 hours. Next the gilts or sows are bred in batches after treated with ovulation-inducing drug(s). The disclosure can effectively alleviate decreased farrowing rate and number of piglets born alive in the batch gilts or sows used the fixed-time artificial insemination, without influencing the serum estrogen level, estrus and ovulation time in mated gilts or sows. Therefore, a novel method for improving the reproductive efficiency of gilts or sows will be established, which is valuable for popularizing batch farrowing in swine including with fixed-time artificial insemination.

7 Claims, 6 Drawing Sheets

Fixed-time artificial insemination:

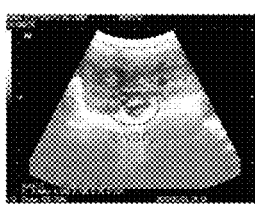 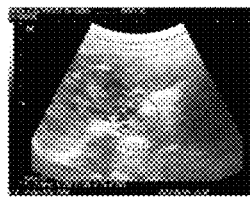 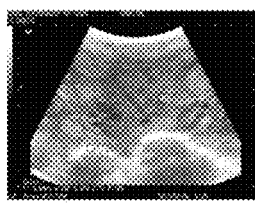

D3 after stopping feeding with Altrenogest   D4 after stopping feeding with Altrenogest   D5-1 after stopping feeding with Altrenogest

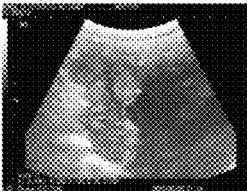 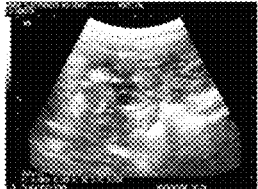 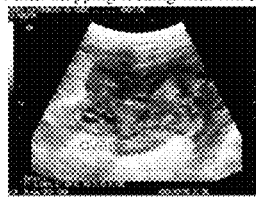

D5-2 after stopping feeding with Altrenogest   D6-1 after stopping feeding with Altrenogest   D6-2 after stopping feeding with Altrenogest

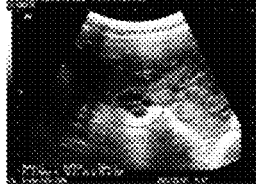  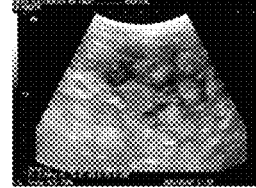 

D7-1 after stopping feeding with Altrenogest   D7-2 after stopping feeding with Altrenogest   D7-3 after stopping feeding with Altrenogest   D8 after stopping feeding with Altrenogest

FIG. 3

Fixed-time artificial insemination+1.5mg letrozole:

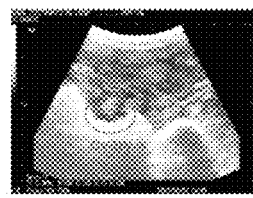  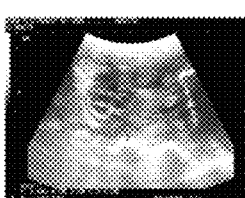

D3 after stopping feeding with Altrenogest   D4 after stopping feeding with Altrenogest   D5-1 after stopping feeding with Altrenogest

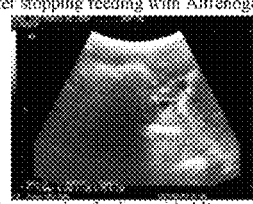 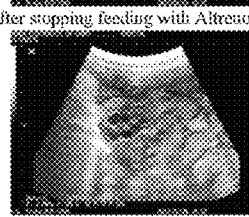 

D5-2 after stopping feeding with Altrenogest   D6-1 after stopping feeding with Altrenogest   D6-2 after stopping feeding with Altrenogest

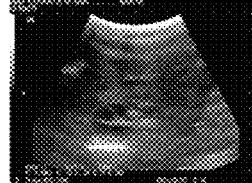 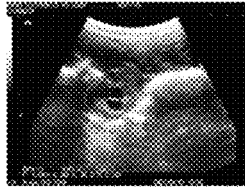 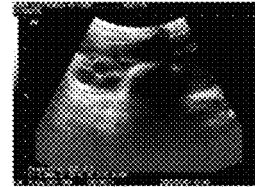 

D7-1 after stopping feeding with Altrenogest   D7-2 after stopping feeding with Altrenogest   D7-3 after stopping feeding with Altrenogest   D8 after stopping feeding with Altrenogest

FIG. 4

Fixed-time artificial insemination+ letrozole （80 μg/kg） :

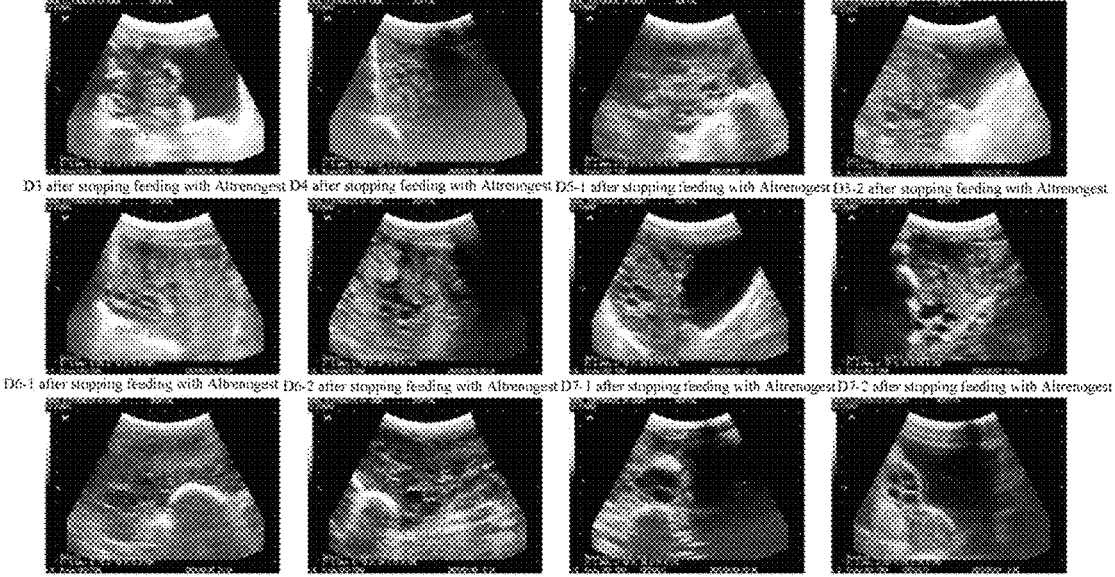

D3 after stopping feeding with Altrenogest  D4 after stopping feeding with Altrenogest  D5-1 after stopping feeding with Altrenogest  D5-2 after stopping feeding with Altrenogest D6-1 after stopping feeding with Altrenogest  D6-2 after stopping feeding with Altrenogest  D7-1 after stopping feeding with Altrenogest  D7-2 after stopping feeding with Altrenogest D7-3 after stopping feeding with Altrenogest  D8-1 after stopping feeding with Altrenogest  D8-2 after stopping feeding with Altrenogest  D10 after stopping feeding with Altrenogest

FIG. 5

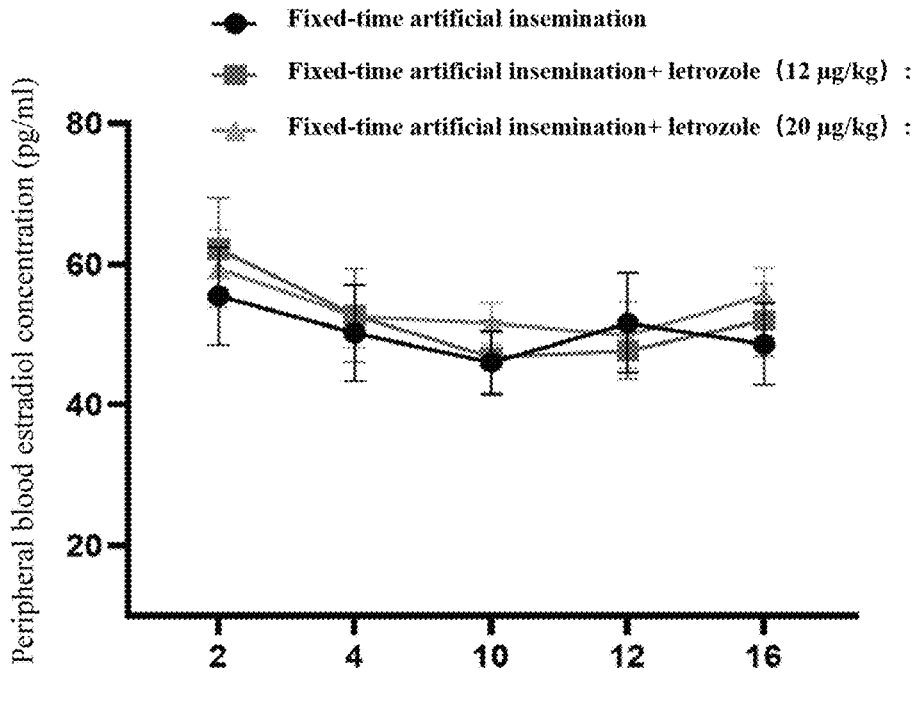

FIG. 6

BATCH MANAGEMENT METHOD FOR IMPROVING FARROWING RATE OR NUMBER OF PIGLETS BORN ALIVE IN SWINE

RELATED APPLICATIONS

The present application claims priority from Chinese Application Number 202410498753.3, filed Apr. 24, 2024, the disclosure of which is hereby incorporated by reference herein in its entirety.

TECHNICAL FIELD

The disclosure relates to the field of multiparous animal reproduction, in particular to a batch management method for improving the farrowing rate or the number born alive in swine and a method for regulating the expression of genes in LPA signalling pathway in a multiparous animal and/or embryo spacing during pregnancy.

BACKGROUND ART

Batch management systems technology, which involves grouping female pigs based on the size of the female pigs population according to a production schedule, replenishing gilts according to the production schedule and using biotechnology to make the gilts and sows of the same batch to achieve the purposes of synchronous estrus, mating and farrowing, is an efficient and controllable management technology system to improve the reproductive performance of the female pigs population in a farm. Compared with the traditional continuous-flow system, the batch farrowing technology can truly realize an "all-in and all-out" strategy in a pig farm, that is, the pigs of the same batch are simultaneously introduced (all-in) into the same pig house and then all released (all-out) after a certain period of time. This mode is helpful to reduce the risk of disease transmission and improve production efficiency and the health level of the pig population. In the all-in and all-out pig farming mode, the pig house can be thoroughly cleaned and disinfected, thus reducing the possibility of disease transmission. In addition, the growth performance of the pig population and the feed utilization rate are also higher. The all-in and all-out pig farming mode has always been the goal pursued by the pig farming industry. With the maturity of reproductive control techniques such as artificial insemination for pigs, estrus synchronization, timed or fixed-timed insemination, and induced synchronous farrowing in order, pig raising and farrowing has gradually achieved a new industrial development situation of batch farrowing and pipeline management. Batch management systems helps to improve production efficiency, ensure a stable supply in the pig farm, and reduce production costs to some extent. By precisely controlling the reproductive cycle of female pigs, the production schedule can be better planned and the non-productive days of female pigs can be reduced, thus greatly improving the production efficiency.

Batch management systems in swine is an efficient and controllable technical system and management system, which involves major reproductive control techniques, such as estrus synchronization, timed or fixed-timed insemination, pregnancy diagnosis, and synchronous farrowing. Appropriate trade-offs can be made by pig farms according to the actual situation and needs. According to the types and quantities of the control techniques used, two types of farrowing can be formed, i.e., precise batch farrowing with precise (traditional) timed insemination (Fixed-Time Artificial Insemination, FTAI) technology as the core, and concise batch farrowing in which Timed-Artificial Insemination (TAI, also referred to as concise Timed-Artificial Insemination) is used (Modern Pig Farming Frontier Technology and Practical Application Series, "Sow Batch Management Technology", China Agriculture Press, ISBN, 978-7-109-29823-1). Precise batch farrowing has synchronous estrus and timed insemination techniques as the core, with highly synchronized female pigs estrus, follicular development and ovulation in combination with techniques such as pregnancy diagnosis and synchronous farrowing, making batch farrowing more accurate and controllable. Compared with the traditional continuous production mode (with daily or weekly heat detection, breeding, farrowing, weaning, and other operations) and concise batch management systems with FTAI (with continuous inspection operations after synchronization of the estrus of female pigs, the subsequent mating time cannot be precisely controlled and the farrowing interval is relatively long), precise batch farrowing can achieve synchronization of various links, such as synchronous estrus, breeding and farrowing in the same batch of sows, can improve the level of bio-safety prevention and control level of the pig farm and the work efficiency, improve the welfare of workers, and even provide an important technical support for the development of the live pig industry in the direction of scale, intensification and industrialization.

During batch management systems, with the Fixed-Time Artificial Insemination technical process, it is possible to achieve synchronized estrus, mating and subsequent farrowing in the same batch of sows. However, sows often face the industrial problems of reduced average number born alive and reduced farrowing rate in the sow population due to the absorption of some or all fetuses during pregnant metaphase, leading to greatly reduced production efficiency of sows, which is also the bottleneck restricting the large-scale popularization and application of this technology (Control of estrus and ovulation: Fertility to timed insemination of gilts and sows, Theriogenology, 2016, 86(6), 1460-1466; Timed Insemination Technology for Sows and Some Existing Problems, Swine Industry Science, 2018, 35(06): 46-48).

The industrial problems present in batch management systems, e.g., low farrowing rate and reduced litter size, are often solved in the prior art by means of nutrition, assisted heat detection of batch procedures, etc. For example, a certain proportion of folic acid is added to the daily ration, but it does not improve the litter size of multiparous sows (Fertility level of sows superovulated at post-weaning estrus. J Anim Sci 1968; 27:709-711). As for the fixed-timed insemination scheme for reserve sows, the applicant has earlier established three schemes, i.e., timed insemination with two-point heat detection, timed insemination with induced estrus and ovulation, and real-time mating with induced estrus, all of which can improve the number born alive piglets. However, the three schemes all increase the number of heat detection and the number of artificial inseminations, and the insemination time cannot be fixed accurately, which enhances the dependence on the technical proficiency of technicians and the workload of the personnel, and fails to achieve the purpose of precisely regulating the sow breeding time and improving work efficiency (Effect of Synchronous Ovulation-Timed Insemination Procedure On Reproductive Performance Of Reserve Sows, Chinese Journal of Animal Science, 2022, 58(08), 235-242). In view of the above reasons, there is an urgent need in the live pig farming industry for an operationally simple and efficient Fixed-Time Artificial Insemination technical process to replace the traditional Fixed-Time Artificial Insemination technical process.

The information in the background art is only for explaining the general background of the disclosure, and should not be regarded as an admission or any form of implication that this information constitutes the prior art well known to those with ordinary skill in the art.

SUMMARY OF THE INVENTION

Pigs are multiparous animal, the number born alive of which is affected by many factors, among which the embryo spacing between embryos is one of the key regulatory factors. When the embryo spacing is too small and the embryos are overcrowded, the subsequent fetal development will be restricted, and some or even all fetuses will be absorbed, resulting in a decrease in the number born alive and the overall farrowing rate in pigs. The applicant researched using mice as animal models and found that during the model process of the batch farrowing with FTAI, the embryo spacing is reduced and the embryos are over-aggregated, leading to a decreased number of embryos born. However, supplementing with a low dose of compound 1-[bis(4-cyanophenyl)alkyl]-1,2,4-triazole to mice and pigs can effectively alleviate the decline in the expression of several key molecules in the LPA signalling pathway, alleviate the excessive aggregation of embryos, and further improve the farrowing rate and the number born alive. The disclosure is completed based even in part on the above findings. Specifically, the disclosure comprises the following content.

In first aspect of the disclosure, there is provided a batch farrowing with FTAI for improving the farrowing rate or the number born alive of female pigs, comprising at least the following steps:

(1) administering an exogenous gonadotropin to a batch of female pigs with synchronized estrus to synchronize follicular development;

(2) further administering 1-[bis(4-cyanophenyl)alkyl]-1,2,4-triazole to the female pigs with synchronicozed follicular development at a range of 6-12 hours after administering the exogenous gonadotropin(s), so as to obtain treated female pigs; and (3) further administering ovulation induction drug(s) to the treated female pigs and performing batch mating.

In some embodiments of the batch farrowing with FTAI for improving the farrowing rate or the number born alive of female pigs according to the disclosure, wherein a batch of gilts are administered with progestogen, or a batch of sows are weaned synchronously to synchronize estrus.

In some embodiments of the batch farrowing with FTAI for improving the farrowing rate or the number born alive of female pigs according to the disclosure, the progestogen including altrenogest is administered in a dosage of 10-30 mg/gilt/day for 10-20 days.

In some embodiments of the batch farrowing with FTAI for improving the farrowing rate or the number born alive of female pigs according to the disclosure, the 1-[bis(4-cyano-phenyl)alkyl]-1,2,4-triazole is fed once or twice at a dosage of 10-50 μg/kg·BW.

In some embodiments of the batch farrowing with FTAI for improving the farrowing rate or the number born alive of female pigs according to the disclosure, wherein the mating time begins at 15-60 hours after ovulation induction hormone is administered.

In some embodiments of the batch farrowing with FTAI for improving the farrowing rate or the number born alive of female pigs according to the disclosure, the fixed-time artificial insemination is carried out multiple times, the first insemination is at 15-26 hours after ovulation induction hormone is administered, and the second insemination is at 10-30 hours after the first insemination.

In some embodiments of the batch farrowing with FTAI for improving the farrowing rate or the number born alive of female pigs according to the disclosure, the exogenous gonadotropin(s) comprise at least one selected from a group consisted of follicle-stimulating hormone, luteinizing hormone, and pregnant mare serum gonadotropin; and the ovulation induction drug comprises at least one of gonadorelin, buserelin, recombinant porcine luteinizing hormone, clomiphene, chorionic gonadotropin, postmenopausal gonadotropin, gonadotrophin releasing hormone, and a in gonadotrophin releasing hormone agonist.

In some embodiments of the batch farrowing with FTAI for improving the farrowing rate or the number born alive of female pigs according to the disclosure, the 1-[bis(4-cyano-phenyl)alkyl]-1,2,4-triazole is administered orally.

In second aspect of the disclosure, there is provided a method for regulating the expression of a gene in an LPA signalling pathway in a multiparous animal, comprising administering 1-[bis(4-cyanophenyl)alkyl]-1,2,4-triazole to the multiparous animal(s).

In third aspect of the disclosure, there is provided a method for regulating embryo spacing in a multiparous animal during pregnancy, comprising administering 1-[bis(4-cyanophenyl)alkyl]-1,2,4-triazole to the multiparous animal(s).

In the disclosure, the results of a large number of creative experiments for comparison of different dosages of 1-[bis(4-cyanophenyl)alkyl]-1,2,4-triazole and different supplementing times have shown that on the premise of not affecting the serum estrogen levels, estrus and ovulation time in female pigs after mating, supplementing with a low dose of 1-[bis(4-cyanophenyl)alkyl]-1,2,4-triazole within a specific time range can effectively alleviate the problems of decreased farrowing rate and reduced number born alive during batch management systems with FTAI, thereby establishing a method for improving the batch production effect in female pigs in conjunction with 1-[bis(4-cyanophe-nyl)alkyl]-1,2,4-triazole, thus providing important value for the popularization and application of batch farrowing with FTAI in swine.

BRIEF DESCRIPTION OF THE DRAWINGS

FIG. 3 shows a dynamic analysis diagram of follicular development in sows during batch farrowing with FTAI, by B-Scan ultrasonic inspection. The ovulation time point is between D7-2 (the circle in the figure indicates the state of large follicles) and D7-3 (the circle in the figure indicates the disappearance of large follicles, indicating that ovulation has been completed) after stopping feeding with altrenogest.

FIG. 4 shows a dynamic analysis diagram of follicular development in sows during batch farrowing with FTAI supplementing with a low dose of 1-[bis(4-cyanophenyl) methyl]-1,2,4-triazole, by B-Scan ultrasonic inspection. In the figure, (1) the supplementing dose of 1-[bis(4-cyano-phenyl)methyl]-1,2,4-triazole is 12 μg/kg·BW; and (2) the ovulation time point is between D7-3 (the circle in the figure indicates the state of large follicles) and D8 (the circle in the figure indicates the disappearance of large follicles, indicating that ovulation has been completed) after stopping feeding with altrenogest.

FIG. 5 shows a dynamic analysis diagram of follicular development in sows during batch farrowing with FTAI supplementing with a high dose of 1-[bis (4-cyanophenyl) methyl]-1,2,4-triazole, by B-Scan ultrasonic inspection. In the figure, (1) the supplementing dose of 1-[bis(4-cyano-phenyl)methyl]-1,2,4-triazole is 80 μg/kg·BW; and (2) on day 10 after stopping feeding with altrenogest, still no ovulation was observed, and ovarian cyst is presented.

FIG. 6 shows that batch farrowing with FTAI in combination with a low dose of 1-[bis(4-cyanophenyl)methyl]-1, 2,4-triazole has no significant effect on the estrogen level of the sows after insemination.

DETAILED DESCRIPTION OF EMBODIMENTS

Figures 1A, 1B, 1C, 1D:
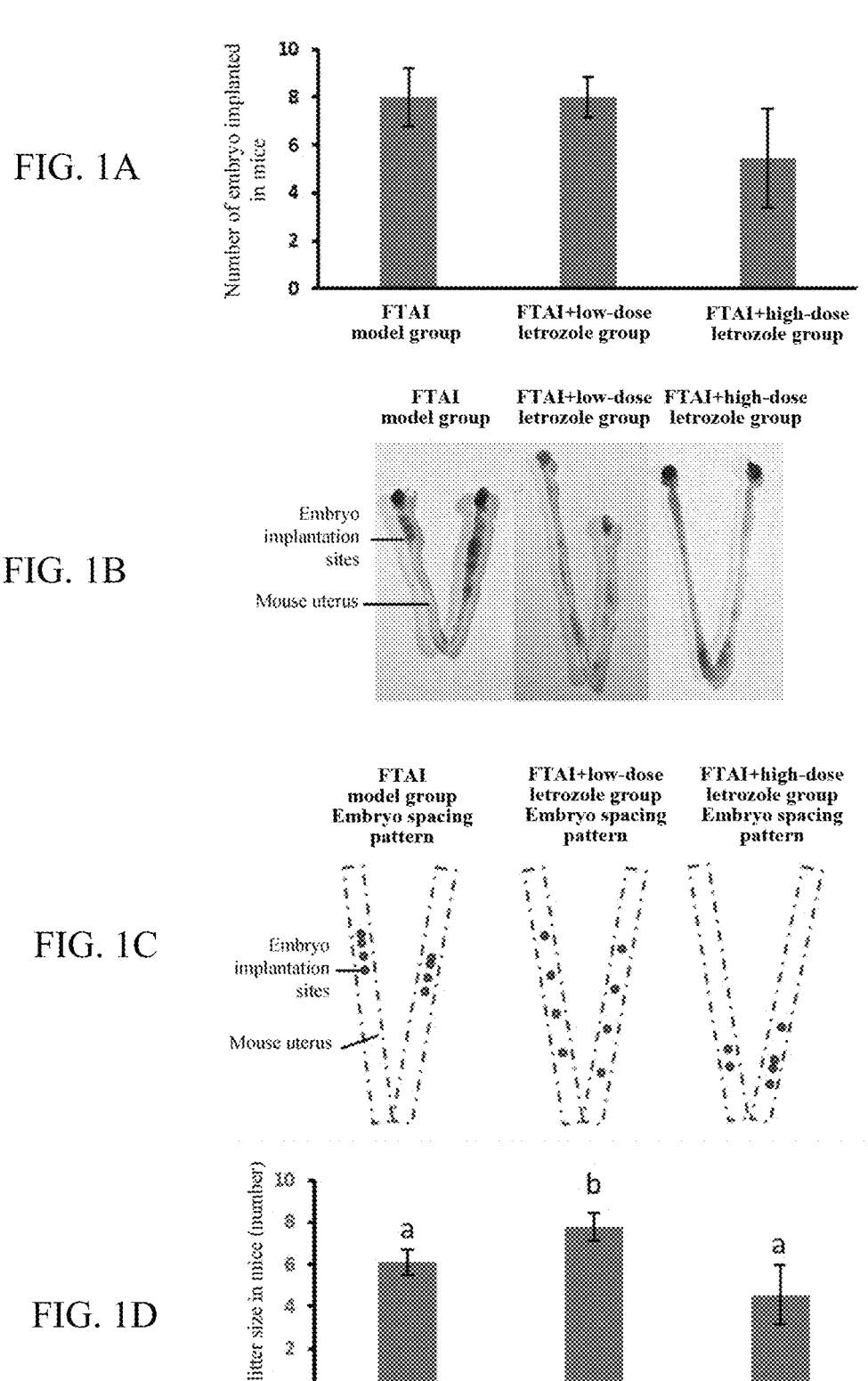
FIGS. 1A-1D shows an analysis diagram of the effect of 1-[bis(4-cyanophenyl)methyl]-1,2,4-triazole on the number of embryo implanted, embryo spacing and number born alive in mice. In the figure: 1A. Compared with mice in a batch farrowing with FTAI model group, 1-[bis(4-cyano-phenyl)methyl]-1,2,4-triazole at a low dose (10 μg/kg·BW) has no significant effect on embryo implantation in mice, whereas 1-[bis(4-cyanophenyl)methyl]-1,2,4-triazole at a high concentration (50 μg/kg·BW) may result in reduced embryo implantation number; 1B. compared with the mice in the batch farrowing model group, 1-[bis(4-cyanophenyl) methyl]-1,2,4-triazole at a low dose (10 μg/kg·BW) results in increased embryo spacing upon embryo implantation in mice, whereas 1-[bis(4-cyanophenyl)methyl]-1,2,4-triazole at a high concentration (50 μg/kg·BW) has no effect on increasing the embryo spacing upon embryo implantation in mice; 1C. patterns of embryo spacing upon embryo implantation in the mice in the batch farrowing model group, batch farrowing+low-dose 1-[bis(4-cyanophenyl)methyl]-1,2,4-triazole (10 μg/kg·BW) model group, and batch farrowing+high-dose 1-[bis(4-cyanophenyl)methyl]-1,2,4-triazole (50 μg/kg·BW) model group; 1D. compared with the mice in the batch farrowing model group, 1-[bis(4-cyanophenyl) methyl]-1,2,4-triazole at the low dose (10 μg/kg·BW) can significantly increase the number born alive in mice, whereas 1-[bis(4-cyanophenyl) methyl]-1,2,4-triazole at the high concentration (50 μg/kg·BW) results in reduced number born alive in mice. Various lowercase letters represent $p < 0.05$.

A number of exemplary embodiments of the disclosure will now be described in detail. The detailed description should not be considered as a limitation on the disclosure, but should be construed as a more detailed description of certain aspects, features and embodiments of the disclosure.

It should be understood that the terminology described in the disclosure is only for describing specific embodiments and is not used to limit the disclosure. In addition, with regard to a numerical range in the disclosure, it should be understood that the upper and lower limits of the range and each intermediate value between them are specifically disclosed. Intermediate values between any stated values or within any stated range as well as any other stated values and every smaller range between intermediate values within the stated range are also included in the disclosure. The upper and lower limits of these smaller ranges can be independently included in or excluded from the range.

Unless otherwise specified, all the technical and scientific terms used herein have the same meanings as commonly understood by those of ordinary skill in the field to which the disclosure belongs. Although the disclosure only describes preferred methods and materials, any methods and materials similar or equivalent to those described herein can also be used in the practice or testing of the disclosure. All documents mentioned in the description are incorporated by reference to disclose and describe methods and/or materials related to the documents. In case of conflict with any incorporated document, the content of the description shall prevail.

The term "batch farrowing", as used herein, refers to the production management of a batch of sows, especially in the pig farming industry, and its core characteristics include synchronous estrus, breeding and farrowing. By dividing the production process into fixed batches, specific production tasks, such as mating and farrowing, are completed within a specific period of time, thus improving production efficiency, reducing costs and facilitating disease prevention and control. In some embodiments, all female animals, such as sows or gilts, are divided into different batches during batch farrowing, and each of the batches is subjected to mating and farrowing according to a predetermined schedule, thus contributing to improving the uniformity of production rhythm, increasing the bio-safety level and reducing the risk of disease transmission.

The term "farrowing rate", as used herein, was calculated as the percentage of the number of farrowed sows divided by the number of mated gilts and sows.

For example, in the case of a certain batch of sows, the farrowing rate=the number of farrowing sows/the number of mated gilts and sows×100%.

The term "Piglet Index (PI)", as used herein, refers to the total number of live piglets born per 100 gilts or sows that have been naturally mated or artificially inseminated. The calculation method is the average number of born alive per litter multiplied by the farrowing rate and then multiplied by the total gilts or sows (100).

Piglet index can be calculated by piglet index =

$$\text{average number of born alive} \times \text{farrowing rate} \times 100.$$

Batch Farrowing Method

In first aspect of the disclosure, there is provided a batch farrowing method for improving the farrowing rate or the number born alive of female pigs, sometimes herein referred to as "the batch farrowing method of the disclosure", comprising the following steps:

(1) administering an exogenous gonadotropin to a batch of gilts or sows with synchronized estrus to synchronize follicular development;
  (2) further administering 1-[bis(4-cyanophenyl)alkyl]-1,2,4-triazole to to the gilts or sows with synchronized follicular development at 6-12 hours after administering the exogenous gonadotropin(s), so as to obtain treated female pigs; and
  (3) further administering ovulation induction drug(s) to the treated female pigs and performing fixed-time artificial insemination.

Alternatively, the method further comprises:

(4) administering progestogen to a batch of gilts, and/or synchronously weaning sows to achieve estrus synchronization in the batch of sows.

It should be understood by those skilled in the art that the above step numbers (1)-(4) are only for the purpose of distinguishing different steps and are not intended to indicate the sequence of steps. As long as the object of the disclosure can be achieved, the sequence of the above steps is not particularly limited. In addition, those skilled in the art should also understand that before and after the above steps (1)-(4) or between any of these steps, other steps or operations may also be included, e.g., further optimizing and/or improving the method described in the disclosure. Each of the steps is described in detail below.

Step (1):

Step (1) in the disclosure is a step of obtaining a batch of sows with synchronized follicular development, which comprises administering the exogenous gonadotropin to the batch of sows with synchronized estrus, with the aim of induction to synchronize follicular development among the batch of sows.

The exogenous gonadotropin in the disclosure is a hormone introduced into an animal by external administration such as oral administration or injection, relative to the hormone secreted or produced by the animal itself. Gonadotropin introduced into the body may also be an artificially synthesized hormone, a natural hormone isolated from an animal, or a combination of an artificially synthesized hormone and a natural hormone. Examples of gonadotropins include, but are not limited to, follicle-stimulating hormone, luteinizing hormone, and chorionic gonadotropin. Gonadotropins may be derived from either animals of the same species or animals of different species. In an exemplary embodiment, for follicular development in sows, a horse-derived hormone, such as pregnant mare serum gonadotropin (PMSG), which is a chorionic gonadotropin of equine animals, can be used.

In the disclosure, the administration route of the exogenous gonadotropin is not limited, and it can be any suitable route, including, for example, intramuscular injection delivery, optionally via intravenous, percutaneous, oral, mucosal, or other methods.

In the disclosure, the administration dosage of gonadotropin is not limited and can be freely selected by those skilled in the art as required. An exemplary administration dosage is 100-10000 IU/animal, preferably 500-9000 IU/animal, more preferably 800-8000 IU/animal, e.g., 1000, 1500, 2000, 2500, 3000, 3500, 4000, 4500, 5000, 5500, 6000, 6500, and 7000 IU/animal. For administration, it can be administered via a single dose or multiple doses.

In the disclosure, the time at which the exogenous gonadotropin is administered is generally between 15 hours and 60 hours after estrus synchronization in a batch of animals such as sows, and the time at which the exogenous gonadotropin is administered may vary depending on the synchronization method. For example, in the case of sows whose estrus are synchronized by administering an exogenous hormone, the time at which the exogenous gonadotropin is further administered is generally 30-60 hours, preferably 35-50 hours, such as 40, 45, or 50 hours, after stopping the administration of the exogenous hormone for estrus synchronization. Still for example, in the case of sows whose estrus are synchronized by weaning the sows, the time at which the exogenous gonadotropin is further administered is generally 20-35 hours, preferably 24-30 hours, such as 24, 25, 26, 27, 28, or 29 hours, after ablactation.

Step (2):

Step (2) in the disclosure involves treating the sows with synchronized follicular development with 1-[bis(4-cyanophenyl)alkyl]-1,2,4-triazole such that under the premise of not affecting the estrus rate, ovulation time, and number of ovulated oocytes in animals, especially multiparous animals such as sows, without causing decreased estrogen level, the embryo spacing upon embryo implantation in multiparous animals is increased, whereby the farrowing rate, number born alive and piglet index of the multiparous animals such as sows are significantly improved.

In the disclosure, 1-[bis(4-cyanophenyl)alkyl]-1,2,4-triazole is a kind of compound with a benzotriazole structure, wherein the alkyl includes C1-C10 alkyl with a linear or branched structure, examples of which include but are not limited to methyl, ethyl, propyl, butyl and pentyl.

In the disclosure, the time at which 1-[bis(4-cyanophenyl)alkyl]-1,2,4-triazole is administered is important for the object of the disclosure, and the administration time is generally 6-12 hours, e.g., 6.5 hours, 7 hours, 7.5 hours, 8 hours, 8.5 hours, 9 hours, 9.5 hours, 10 hours, 10.5 hours, 11 hours, and 11.5 hours, after the exogenous gonadotropin is administered. 1-[Bis (4-cyanophenyl)alkyl]-1,2,4-triazole can be administered at least once within the above time range, and optionally, it can be administered multiple times within the above time range.

In the disclosure, the administration dosage of 1-[bis(4-cyanophenyl)alkyl]-1,2,4-triazole is generally 10-50 μg/kg·BW administered in a single dose, preferably 12-30 μg/kg·BW administered in a single dose, further preferably 12-25 μg/kg·BW administered in a single dose, e.g., 13, 14, 15, 16, 17, 18, 19, 20, 21, 22, or 23 μg/kg·BW. Alternatively, it can be administered in two doses. As long as the total administration dosage of the two doses is within a range of 10-50 μg/kg·BW, the dosage of each administration is not particularly limited, for example, each administration dosage is generally within a range of 1-40 μg/kg·BW. In the case of two doses, the time interval between the two instances of administration is 8-30 hours, preferably 9-28 hours, more preferably 10-26 hours, further preferably 12-25 hours, 14-24 hours, etc. If the administration dosage is too high, it tends to affect the estrus and ovulation in animals and even cause ovarian cysts. The administration dosage of the disclosure is important. From a previous experiment of feeding batch farrowing sows with different doses of 1-[bis(4-cyanophenyl)methyl]-1,2,4-triazole at different times, it has been found that with reference to the application dosage and oral administration time in clinical medicine and bovine superovulation, 1-[bis(4-cyanophenyl)methyl]-1,2,4-triazole may cause problems such as recessive estrus, ovarian cyst, anovulation, and pregnancy failure in sows. Therefore, existing applications in human clinical medicine and bovine superovulation cannot be used to give the suggestion that 1-[bis(4-cyanophenyl)methyl]-1,2,4-triazole improves the number born alive during batch farrowing in swine.

In the disclosure, the mode of administration of 1-[bis(4-cyanophenyl)alkyl]-1,2,4-triazole is not limited, and it can be any suitable mode, including, for example, intramuscular injection delivery, optionally via intravenous, percutaneous, oral, mucosal, or other methods. In some embodiments, 1-[bis(4-cyanophenyl)alkyl]-1,2,4-triazole of the disclosure is administered orally.

Step (3):

Step (3) in the disclosure is an ovulation induction and insemination step, which comprises further administering an ovulation induction drug to the treated gilts or sows and performing fixed-time artificial insemination.

In the disclosure, ovulation induction can be carried out by administering drugs, and such drugs are known in the art, including synthesized compounds and also natural compounds isolated from animals, examples of which include, but are not limited to, gonadorelin, buserelin, recombinant porcine luteinizing hormone, clomiphene, chorionic gonadotropin, postmenopausal gonadotropin, gonadotrophin releasing hormone, and gonadotrophin releasing hormone agonists. In the disclosure, one of or a combination of some of the above substances can be used.

In the disclosure, the administration timing of the ovulation induction drug is generally interval a specific time after the administration of an exogenous gonadotropin or when the animal is in estrus, and the specific time is generally 10-200 hours, preferably 20-180 hours, more preferably 30-160 hours, further preferably 40-140 hours, such as 50 hours, 60 hours, 70 hours, 80 hours, 90 hours, 100 hours, and 120 hours.

In the disclosure, the administration dosage of the ovulation induction drug is generally 40-300 ug/animal, preferably 50-250 ug/animal, further preferably 70-200 ug/animal, such as 80 ug/animal, 90 ug/animal, 100 ug/animal, 120 ug/animal, 140 ug/animal, 160 ug/animal, and 180 ug/animal.

In the disclosure, after the ovulation induction drug is administered, the batch mating is carried out, and the mating is generally carried out by means of timed insemination. Timed insemination is generally carried out manually, and generally at 10-80 hours, preferably 15-70 hours, further preferably 15-60 hours, such as 20, 30, 40, 50, 60, and 70 hours, after the ovulation induction drug is administered. Timed insemination can be performed once, preferably twice or more. The time interval between two timed inseminations is generally 10-20 hours, such as 12, 14, 16, 18 and 20 hours.

In some embodiments, the batch mating in the disclosure is performed by means of two timed inseminations, wherein the first insemination is performed at 20-26 hours, preferably 22-24 hours, after the ovulation induction hormone is administered, and the second insemination is performed at 10-30 hours, preferably 15-25 hours, more preferably 16-20 hours after the first mating.

Step (4):

Step (4) in the disclosure is a step of estrus synchronization in a batch of female animals, thereby obtaining a batch of female animals such as sows with synchronized estrus, which is an optional step in the disclosure, and includes administering such as progestogen(s) to a batch of reserve animals, such as gilts, or synchronously weaning parous female animals, such as sows, to achieve estrus synchronization in the batch of animals.

In the disclosure, examples of progestogen include, but are not limited to, altrenogest, and the administration dosage thereof is generally 10-30 mg/animal/day, such as 15-28 mg/animal/day, 16-25 mg/animal/day, 18-23 mg/animal/day, 19 mg/animal/day, 20 mg/animal/day, 21 mg/animal/day, and 22 mg/animal/day. The frequency of administration may be once, more generally multiple times, e.g., once a day, for 5-30 days, preferably 6-28 days, 7-26 days, 8-24 days, and 9-22 days, such as 10 days, 11 days, 12 days, 13 days, 14 days, 15 days, 16 days, 17 days, 18 days, 19 days, and 20 days. In the disclosure, the mode of administration of progestogen is not limited, and is, for example, intramuscular injection, via intravenous, percutaneous, oral, mucosal, or other methods.

Method for Regulating Gene Expression

In second aspect of the disclosure, there is provided a method for regulating the expression of a gene in an LPA signalling pathway in a multiparous animal, sometimes herein referred to as "the gene regulation method of the disclosure", comprising administering 1-[bis(4-cyanophenyl)alkyl]-1,2,4-triazole to the multiparous animal.

In the disclosure, it is discovered that 1-[bis(4-cyanophenyl)alkyl]-1,2,4-triazole can cause a change in the expression of a gene in an LPA signalling pathway in a multiparous animal. For multiparous animals in natural estrus, especially female animals such as female pigs, the expression of a gene in the LPA signalling pathway in the uterus of the multiparous animal decreases in traditional farrowing methods involving administering an exogenous hormone. In the gene regulation method of the disclosure, the expression of the gene in the LPA signalling pathway is up-regulated, enhanced or increased by administering 1-[bis(4-cyanophenyl)alkyl]-1,2,4-triazole to a multiparous animal, especially a female animal for batch farrowing.

In some embodiments, 1-[bis(4-cyanophenyl)alkyl]-1,2,4-triazole is administered between the administration of an exogenous gonadotropin and an ovulation induction hormone such as an exogenous gonadotrophin releasing hormone. Preferably, 1-[bis(4-cyanophenyl)alkyl]-1,2,4-triazole is administered 7-9 hours after the exogenous gonadotropin is administered.

In the disclosure, the gene in the LPA signaling pathway is not particularly limited, and examples thereof include, but are not limited to, Enpp2, Lpar3, and ptgs2. Among them, Enpp2 gene is the gene for the expression of ATX, the key enzyme of LPA synthesis, Lpar3 gene is LPA receptor gene, and ptgs2 gene are a key gene downstream of LPAR.

In the disclosure, the expression of the gene in the LPA signaling pathway includes gene transcription into an mRNA and/or translation into a corresponding protein. Therefore, the regulation of gene expression includes the regulation at mRNA level and/or protein level.

From the research of the disclosure, it has been discovered that the LPA signaling pathway plays a key role during the regulation of the embryo spacing in pigs or mice. In the precise batch farrowing mode, the expression levels of the several key molecules ATX (key enzyme for LPA synthesis), LPAR (receptor for LPA functioning), and PTGS2 (a key molecule downstream of LPA signalling, rate-limiting enzyme for prostaglandin synthesis) molecules in the LPA signalling pathway in the uterus of the female mice (simulating the process of batch farrowing with FTAI) and pigs are abnormally reduced. In the method of the disclosure, the embryo spacing is regulated by up-regulating, enhancing or increasing the expression of the genes in the LPA signalling pathway.

Method for Regulating Embryo Spacing

In third aspect of the disclosure, there is provided a method for regulating embryo spacing in a multiparous animal during pregnancy, sometimes herein referred to as "the embryo spacing regulating method of the disclosure", comprising administering 1-[bis(4-cyanophenyl)alkyl]-1,2, 4-triazole to the multiparous animal.

In the disclosure, from the research on mouse models and the batch farrowing process of female pigs, it has been discovered that after administering 1-[bis(4-cyanophenyl) alkyl]-1,2,4-triazole to a multiparous animal, over-intensive embryo spacing can be effectively avoided, thereby ameliorating the consequent decline in farrowing rate and piglet index of pigs.

In the disclosure, preferably, 1-[bis(4-cyanophenyl)alkyl]-1,2,4-triazole is used in combination with exogenous hormones and exogenous gonadotropins and ovulation induction hormones. For example, 1-[bis(4-cyanophenyl) alkyl]-1,2,4-triazole is administered between the administration of an exogenous gonadotropin and an ovulation induction hormone such as an exogenous gonadotrophin releasing hormone. Preferably, 1-[bis(4-cyanophenyl)alkyl]-1,2,4-triazole is administered 7-9 hours after the exogenous gonadotropin is administered.

EXAMPLE 1

In this example, a mouse model was used to study the effect of the treatment with 1-[bis(4-cyanophenyl)methyl]-1,2,4-triazole on the spacing between embryo sites in multiparous animals after implantation and on the expression of key genes regulating the spacing between embryo sites.

6-8-week-old ICR female mice acclimatized to the laboratory mouse house environment and in a good condition were selected and divided into a batch farrowing with FTAI model group, a batch farrowing with FTAI+low-dose model group, and a batch farrowing with FTAI+high-dose model group, and 10IU PMSG was injected at 17:00 pm. At 6-8 hours after a single injection of PMSG to the batch farrowing with FTAI+low-dose model group and the batch farrowing with FTAI+high-dose model group, respectively, the groups were supplemented with a low dose of 1-[bis(4-cyanophenyl)methyl]-1,2,4-triazole (10 μg/kg·BW) and a high dose of 1-[bis(4-cyanophenyl)methyl]-1,2,4-triazole (50 μg/kg·BW), respectively, and at 46-48 hours after the injection of PMSG, the groups were then injected with prepared 10IU GnRH and then put into a breeding male mouse cage. At 7:00-9:00 the next morning, vaginal plugs were examined, and this day was recorded as day 1 (D1) of pregnancy. In the afternoon of day 5 (D5) of pregnancy, 0.4 ml of 1% Chicago blue-normal saline solution was injected into model mice at the caudal vein, and after 3 minutes of systemic circulation, the mice were sacrificed by means of cervical dislocation, the abdominal cavity was immediately cut open, and the abdominal aorta was cut for bleeding. Then, uteri and ovaries were removed with surgical ophthalmic scissors, immersed in physiological saline for washing, and then put into a 4% paraformaldehyde fixation solution for 5 minutes of morphological fixation. Blue dots on the uterus were recorded as embryo implantation sites, the number of implantation sites was counted, and patterns of embryo spacing in different groups were drawn.

For some of the mice treated above, no intermediate test was done, and after the mice gave birth, the number born alive in each group was counted.

The results showed that there was no significant difference in the embryo implantation number between the batch farrowing with FTAI+compound model group and the batch farrowing with FTAI model group, but the low dose of the compound (10 μg/kg·BW) could effectively alleviate the overcrowding of embryos and increase the spacing between embryos, whereas the high dose of the compound (50 μg/kg·BW) could not alleviate the overcrowding of embryos. In addition, compared with the mice in the batch farrowing with FTAI model group, the low dose of the compound (10 μg/kg·BW) could significantly increase the number born alive in mice, whereas the high concentration of the compound (50 μg/kg·BW) resulted in decreased number born alive in mice (see FIGS. 1A-1D).

Unfixed uteri were isolated for RNA extraction, reverse transcription and quantitative PCR detection of several key target molecules in the LPA signalling pathway, i.e., detection of Enpp2 (a gene for the expression of ATX, the key enzyme of LPA synthesis), Lpar3 (LPA receptor gene), and ptgs2 (a key gene downstream of LPAR). In the control group, female mice were in natural estrus and mated with male mice.

Figure 2:
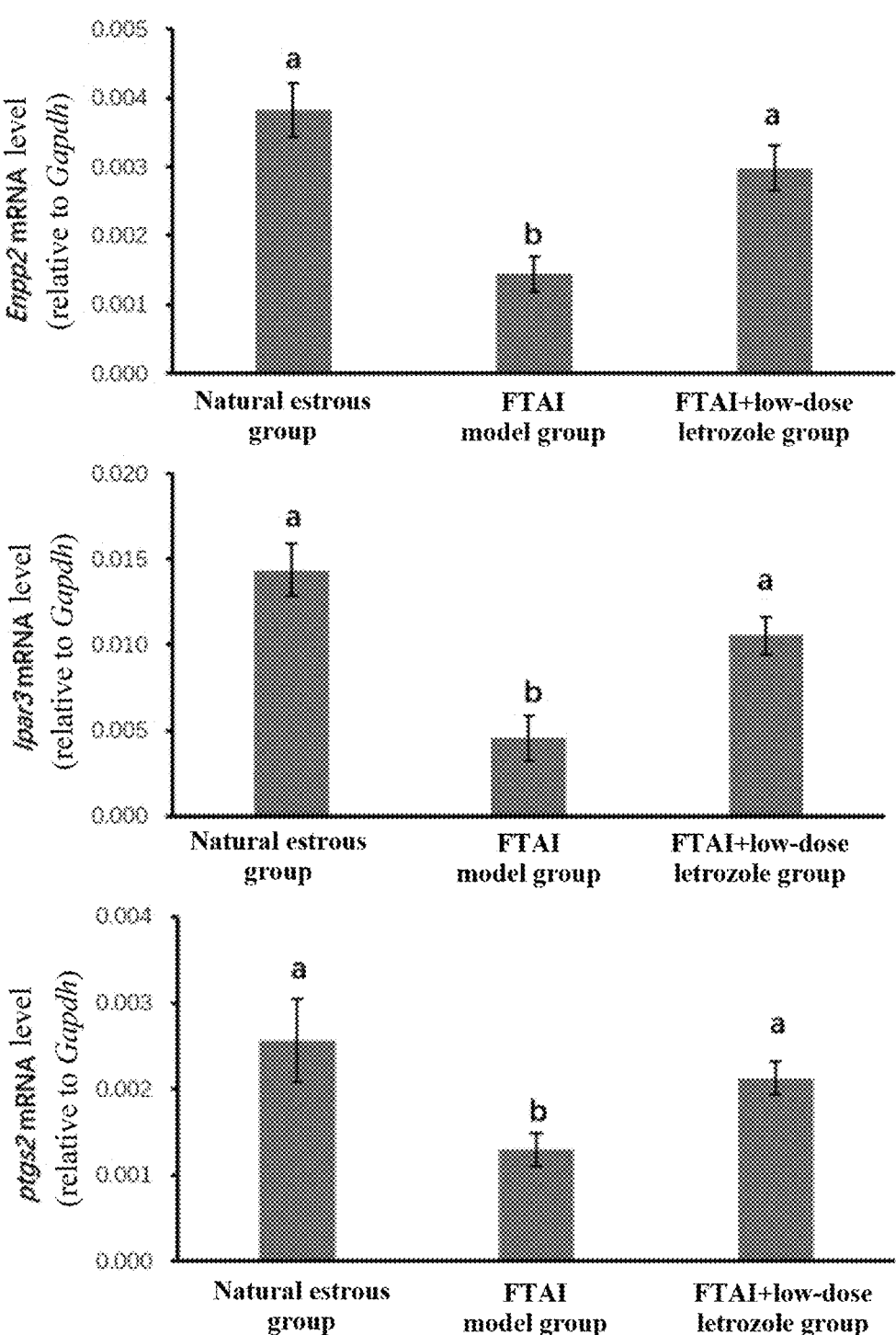
FIG. 2 shows the regulation of the expression of key molecules in the LPA signalling pathway in the uterus of mice by 1-[bis(4-cyanophenyl)methyl]-1,2,4-triazole. The supplementing concentration of 1-[bis(4-cyanophenyl) methyl]-1,2,4-triazole is 10 μg/kg·BW. Different lowercase letters represent significant ($P < 0.05$).

Compared with the natural estrus group, the batch farrowing with FTAI model group had significantly decreased Enpp2, Lpar3 and ptgs2 mRNA levels, whereas the levels thereof in the uteri of the mice in the batch farrowing with FTAI model+1-[bis(4-cyanophenyl)methyl]-1,2,4-triazole simulation group had no significant difference from those in the natural estrus group, but were significantly higher than those in the batch farrowing with FTAI model group (FIG. 2).

EXAMPLE 2

Effect of Treatment with Different Doses of 1-[bis (4-cyanophenyl)methyl]-1,2,4-triazole on Sow Estrus and Ovulation (1) Experimental Method and Grouping Landrace x Large White reserve sows, about 230 days old, were randomly divided into a batch farrowing with FTAI and batch farrowing with FTAI combined with different doses of 1-[bis(4-cyanophenyl)methyl]-1,2,4-triazole groups, and during the experiment, the experimental animals in each group were fed regularly and gained free access to water according to the requirements of feeding management in the farm.

Referring to the dosage of 1-[bis(4-cyanophenyl)methyl]-1,2,4-triazole in clinical medicine and using standard weight-dosage conversion, the recommended dosage of 1-[bis(4-cyanophenyl)methyl]-1,2,4-triazole for sows was 50-150 μg/kg·BW/day, orally for consecutive 5 days, as derived by conversion. In addition, the applicant previously studied uniparous cows, and in the ovulation induction scheme, the reference dosage of 1-[bis(4-cyanophenyl) methyl]-1,2,4-triazole was 60-200 μg/kg·BW, administered in a single dose; furthermore, by means of conversion in conjunction with the dosage for model animals (mice) previously in the laboratory, various dosages were designed. The treatment methods of hormones and drugs for sows in each group were as follows:

batch farrowing with FTAI: the sows were fed with an altrenogest oral solution at 20 mg/animal at the same time every day, for 18 days; PMSG at 1000 IU/animal was injected intramuscularly 42 h after the last feeding with altrenogest, GnRH at 100 μg/animal was injected intramuscularly 80 h after the injection of PMSG, a first timed insemination was performed 24 h after the injection of GnRH, and a second timed insemination was performed 16 h after the first insemination.

Treatment group 1: the hormone treatment and mating schemes for gilts were the same as FTAI. The difference lay in that PMSG at 1000 IU/gilt was injected intramuscularly 42 h after the last feeding with altrenogest, and 1-[bis(4-cyanophenyl)methyl]-1,2,4-triazole at 12 μg/kg·BW/day was administered orally 8 h after the injection of PMSG, for 1 day.

Treatment group 2: the hormone treatment and mating schemes for gilts were the same as FTAI. The difference lay in that PMSG at 1000 IU/gilt was injected intramuscularly 42 h after the last feeding with altrenogest, and 1-[bis(4-cyanophenyl)methyl]-1,2,4-triazole at 12 μg/kg·BW/day was administered orally 8 h after the injection of PMSG, for 2 days.

Treatment group 3: the hormone treatment and mating schemes for gilts were the same as FTAI. The difference lay in that PMSG at 1000 IU/gilt was injected intramuscularly 42 h after the last feeding with altrenogest, and 1-[bis(4-cyanophenyl)methyl]-1,2,4-triazole at 20 μg/kg·BW/day was administered orally 8 h after the injection of PMSG, for 1 day.

Treatment group 4: the hormone treatment and mating schemes for sows were the same as FTAI. The difference lay in that PMSG at 1000 IU/gilt was injected intramuscularly 42 h after the last feeding with altrenogest, and 1-[bis (4-cyanophenyl)methyl]-1,2,4-triazole at 20 μg/kg·BW/day was administered orally 8 h after the injection of PMSG, for 2 days.

Treatment group 5: the hormone treatment and mating schemes for gilts were the same as FTAI. The difference lay in that PMSG at 1000 IU/animal was injected intramuscularly 42 h after the last feeding with altrenogest, and 1-[bis(4-cyanophenyl)methyl]-1,2,4-triazole at 20 μg/kg·BW/day was administered orally 8 h after the injection of PMSG, for 3 days.

Treatment group 6: the hormone treatment and mating schemes for gilts were the same as FTAI. The difference lay in that PMSG at 1000 IU/animal was injected intramuscularly 42 h after the last feeding with altrenogest, and 1-[bis(4-cyanophenyl)methyl]-1,2,4-triazole at 20 μg/kg·BW/day was administered orally 8 h after the injection of PMSG, for 5 days.

Treatment group 7: the hormone treatment and mating schemes for gilts were the same as FTAI. The difference lay in that PMSG at 1000 IU/animal was injected intramuscularly 42 h after the last feeding with altrenogest, and 1-[bis(4-cyanophenyl)methyl]-1,2,4-triazole at 40 μg/kg·BW/day was administered orally 8 h after the injection of PMSG, for 1 day.

Treatment group 8: the hormone treatment and mating schemes for gilts were the same as FTAI. The difference lay in that PMSG at 1000 IU/animal was injected intramuscularly 42 h after the last feeding with altrenogest, and 1-[bis(4-cyanophenyl)methyl]-1,2,4-triazole at 40 μg/kg·BW/day was administered orally 8 h after the injection of PMSG, for 5 days.

Treatment group 9: the hormone treatment and mating schemes for gilts were the same as FTAI. The difference lay in that PMSG at 1000 IU/animal was injected intramuscularly 42 h after the last feeding with altrenogest, and 1-[bis(4-cyanophenyl)methyl]-1,2,4-triazole at 80 μg/kg·BW/day was administered orally 8 h after the injection of PMSG, for 5 days.

Treatment group 10: the hormone treatment and mating schemes for gilts were the same as FTAI. The difference lay in that PMSG at 1000 IU/animal was injected intramuscularly 42 h after the last feeding with altrenogest, and 1-[bis (4-cyanophenyl)methyl]-1,2,4-triazole at 160 μg/kg·BW/day was administered orally 8 h after the injection of PMSG, for 5 days.

(2) Monitoring of Dynamic Changes of Follicles by B-Scan Ultrasonic Inspection and Determination of Ovulation Time a. The B-Scan ultrasonic inspection instrument used was HS-1600V (Honda Electronics, Japan).

b. B-Scan ultrasonic inspection: Sows were fixed in a crate. The operator for B-Scan ultrasonography stood at the position where the sow was well fixed, placed a B-Scan ultrasonographical probe coated with a coupling agent 5 cm right above the penultimate pair of nipples of the sow, with the probe pointing to the center of the body of the sow for sector scanning.

c. Judgment of follicular ovulation or cyst:

Determination of ovulation time: After follicles reached the ovulation diameter, if the number of large follicles in the ovary was significantly reduced as monitored by B-Scanultrasonography, but there were still three follicles with the ovulation diameter (6.5 mm), this time point was taken as the ovulation time; and if disappearance of large follicles on the ovary was monitored by B-Scan ultrasonography, the middle point between two examinations by B-Scan ultrasonography was recorded as the ovulation time (J. M. G Santos, Brazil, 2004; J. J. J. van Leeuwen, Wageningen, The Netherlands, 2011).

Determination of ovarian cyst: At present, there were different definitions of ovarian cyst. Waberski D et al. (1999) believed that the follicle diameter exceeded 11 mm, Knox RV et al. (2004) believed that it exceeded 12 mm, and Cezar Dobler Castagna et al. (2004) believed that it exceeded 20 mm. In conjunction with the literature and the results of the B-Scan ultrasonographical image in the disclosure, the judgment was based on an abnormal follicular state in which the follicle diameter was too large and lasted for more than 10 days or longer, and the whole ovary had no obvious corpus luteum structure.

(3) Heat Detection in Pigs

The next day after stopping feeding with altrenogest, the sows were inspected. The heat detection in pigs was indicated as a standing reflex in response to the manual application of pressure to the gilts or sows back, together with purplish red labial mucosa and rich and thick mucus secretion. The sows were detected twice a day, in the morning and afternoon, estrous sows were marked on the back, and the estrus time was recorded.

Standing reflex, is identified by signs such as swelling and reddening of the vulva, vulvar discharge, vocalization, inappetance, boar seeking behaviour, ear popping and standing for back pressure. Gilts should be bred 12-24 hours after heat is detected, and again 12 hours later. Sows should be bred 24-36 hours after detection of heat, and again 12 hours after the first insemination.

(4) Experimental Results

In this example, the estrus rate in the gilts supplemented with a low dose of 1-[bis(4-cyanophenyl)methyl]-1,2,4- triazole (treatment groups 1, 2, 3, 4, 5, and 7) was not significantly different from the estrus rate in the gilts for FTAI group, whereas those supplemented with a high dose of 1-[bis(4-cyanophenyl)methyl]-1,2,4-triazole or with multiple (5) low doses of 1-[bis(4-cyanophenyl)methyl]-1,2,4-triazole (treatment groups 6, 8, 9, and 10) showed decreased estrus rate or even no estrus. In the treatment groups fed with 1-[bis(4-cyanophenyl)methyl]-1,2,4-triazole at 80 $\mu$g/kg·BW/day and 160 $\mu$g/kg·BW/day for 5 consecutive days (treatment groups 9 and 10), the gilts still exhibited no estrus on the 8th day after altrenogest was stopped (Table 1).

2). B-scan ultrasonic inspection analysis images (FIGS. 3, 4, and 5) respectively exhibited the dynamic development process of follicles in batch farrowing with FTAI, batch farrowing with FTAI in combination with low-dose (12 $\mu$g/kg·BW) 1-[bis(4-cyanophenyl)methyl]-1,2,4-triazole, and batch farrowing with FTAI in combination with high-dose (80$\mu$g/kg·BW) 1-[bis(4-cyanophenyl)methyl]-1,2,4-triazole, wherein the sows in the batch farrowing with FTAI and those in the batch farrowing with FTAI in combination with low-dose (12 $\mu$g/kg·BW) 1-[bis(4-cyanophenyl)methyl]-1,2,4-triazole could both ovulate normally, whereas

TABLE 1

Effects of treatments with different doses of compound on estrus rate and estrus time in gilts

| Grouping | Sample size | Estrus number | Estrus rate (%) | Interval from stopping taking Altrenogest to estrus (days) | Number of estrous animals at different times after stopping Altrenogest (day/animal) | | | | | | | |
|---|---|---|---|---|---|---|---|---|---|---|---|---|
| | | | | | 4.5 | 5 | 5.5 | 6 | 6.5 | 7 | 7.5 | 8 |
| Precise | 39 | 35 | 89.74[a] | 6.10 ± 0.07[b] | 1 | 0 | 11 | 12 | 5 | 4 | 0 | 2 |
| Treatment group 1 | 30 | 27 | 90.00[a] | 6.13 ± 0.12[b] | 0 | 1 | 8 | 8 | 4 | 5 | 1 | 0 |
| Treatment group 2 | 27 | 23 | 85.19[a] | 6.07 ± 0.13[b] | 0 | 0 | 9 | 7 | 3 | 3 | 1 | 0 |
| Treatment group 3 | 25 | 22 | 88.00[a] | 6.11 ± 0.12[b] | 0 | 0 | 7 | 7 | 5 | 2 | 1 | 0 |
| Treatment group 4 | 25 | 21 | 84.00[a] | 6.07 ± 0.15[b] | 0 | 0 | 8 | 6 | 4 | 2 | 1 | 0 |
| Treatment group 5 | 26 | 24 | 92.31[a] | 6.19 ± 0.16[b] | 0 | 2 | 6 | 7 | 3 | 3 | 2 | 1 |
| Treatment group 6 | 26 | 20 | 76.92[b] | 6.70 ± 0.16[a] | 0 | 1 | 0 | 5 | 3 | 8 | 1 | 2 |
| Treatment group 7 | 26 | 22 | 84.61[a] | 6.77 ± 0.14[a] | 0 | 0 | 2 | 2 | 9 | 0 | 9 | 0 |
| Treatment group 8 | 24 | 4 | 16.67[b] | 6.25 ± 0.14[b] | 0 | 0 | 0 | 2 | 2 | 0 | 0 | 0 |
| Treatment group 9 | 24 | 0 | 0.00[b] | — | — | — | — | — | — | — | — | — |
| Treatment group 10 | 24 | 0 | 0.00[b] | — | — | — | — | — | — | — | — | — |

Note:
Various lowercase letters indicated significant differences in various indexes than the sows in the batch farrowing with FTAI, P < 0.05.

The follicular development in the gilts in each of the different treatment groups was dynamically monitored by B-scan ultrasonography, and the ovulation time was estimated. There was no significant difference between the ovulation time in the treatment groups (1, 2, 3, and 5) and the gilt estrus time in the batch farrowing with FTAI. With the increase of the dosage of 1-[bis(4-cyanophenyl)methyl]-1,2,4-triazole, the time from stopping taking altrenogest to ovulation was prolonged, and the number of ovarian cysts increased. In the treatment groups fed with 1-[bis(4-cyanophenyl)methyl]-1,2,4-triazole at 80 $\mu$g/kg·BW/day and 160 $\mu$g/kg·BW/day for 5 consecutive days (treatment groups 9 and 10), the sows still did not ovulate for 10 days after stopping taking altrenogest and had a cyst problem (Table the follicles in the sows in the batch farrowing with FTAI in combination with high-dose (80 $\mu$g/kg·BW) 1-[bis(4-cyanophenyl)methyl]-1,2,4-triazole showed no ovulation and were presented as cyst.

These results showed that high-dose 1-[bis(4-cyanophenyl)methyl]-1,2,4-triazole not only inhibited estrus and ovulation in sows, but also even caused ovarian cysts. In the batch farrowing with FTAI in combination with low-dose 1-[bis(4-cyanophenyl)methyl]-1,2,4-triazole, there was no significant change in gilt estrus rate and ovulation time, and also no ovarian cyst was caused.

TABLE 2

Effects of treatments with different doses of compound on ovulation in gilts

| Grouping | Sample size | Number of animals with ovulation | Interval from stopping taking Altrenogest to ovulation (h) | Number of animals with ovarian cyst | Cyst ratio (%) |
|---|---|---|---|---|---|
| Precise | 39 | 35 | 167.06 ± 3.61[a] | 2 | 5.13[a] |
| Treatment group 1 | 30 | 27 | 170.13 ± 3.87[a] | 0 | 0.00[b] |
| Treatment group 2 | 27 | 23 | 172.15 ± 3.34[a] | 0 | 0.00[b] |
| Treatment group 3 | 25 | 22 | 169.57 ± 2.19[a] | 0 | 0.00[b] |
| Treatment group 4 | 25 | 21 | 194.25 ± 2.96[b] | 0 | 0.00[b] |
| Treatment group 5 | 26 | 24 | 177.79 ± 4.75[a] | 3 | 11.53[c] |
| Treatment group 6 | 26 | 20 | 187.67 ± 3.69[b] | 4 | 15.38[c] |
| Treatment group 7 | 26 | 22 | 191.50 ± 5.74[b] | 3 | 11.53[c] |
| Treatment group 8 | 24 | 4 | 210.00 ± 2.65[b] | 19 | 79.17[c] |
| Treatment group 9 | 24 | 0 | — | 24 | 100.00[c] |
| Treatment group 10 | 24 | 0 | — | 24 | 100.00[c] |

Note:
Various lowercase letters indicated significant differences in various indexes than the gilts in the batch farrowing with FTAI, P < 0.05.

EXAMPLE 3

In this example, the effect of 1-[bis(4-cyanophenyl)methyl]-1,2,4-triazole on the farrowing rate and the number born alive from the gilts in the batch farrowing with FTAI was studied.

(1) Experimental Method and Grouping

The breed of the gilts used in this example was Landrace x Large White binary sows, the reserve sows were randomly divided into the following 4 groups, and the treatment method for each group was as follows:

batch farrowing with FTAI: the sows were fed with an altrenogest oral solution at 20 mg/gilt at the same time every day, for 18 days; PMSG at 1000 IU/gilt was injected intramuscularly 42 h after the last feeding with altrenogest, GnRH at 100 µg/gilt was further injected intramuscularly 80 h after the intramuscular injection of PMSG, a first timed insemination was performed 24 h after the injection of GnRH, and a second timed insemination was performed after 24 h.

Treatment group 1 (batch farrowing with FTAI, with supplementing with 1-[bis(4-cyanophenyl)methyl]-1,2,4-triazole (12 µg/kg·BW, orally once)): The hormone treatment and mating schemes for gilts were the same as those for gilts in the batch farrowing with FTAI. The gilts were administered orally once with 1-[bis(4-cyanophenyl)methyl]-1,2,4-triazole at 12 µg/kg·BW 8 h after the injection of PMSG.

Treatment group 2 (batch farrowing with FTAI, with supplementing with 1-[bis (4-cyanophenyl)methyl]-1,2,4-triazole (12 µg/kg·BW, orally twice)): The hormone treatment and mating schemes for gilts were the same as those for gilts in the batch farrowing with FTAI. The gilts were administered orally once with 1-[bis(4-cyanophenyl)methyl]-1,2,4-triazole at 12 µg/kg·BW 8 h after the injection of PMSG, and then orally once with 1-[bis(4-cyanophenyl)methyl]-1,2,4-triazole at 12 µg/kg·BW after another 24 h.

Treatment group 3 (batch farrowing with FTAI, supplemented with 1-[bis(4-cyanophenyl)methyl]-1,2,4-triazole (20 µg/kg·BW, orally in a single dose)): The hormone treatment and mating schemes for gilts were the same as those for gilts in the batch farrowing with FTAI. The gilts

(2) Statistics of Estrus Time, Estrus, Pregnancy and Farrowing in Sows in Each Group The farrowing rate and piglet index of sows in the different treatment groups were calculated as follows:

farrowing rate in sows = number of farrowing sows/the number of mated sows × 100%; and piglet index = number born alive × farrowing rate × 100, wherein Piglet Index (PI), a comprehensive index to measure the overall reproductive performance of a sow population at present in production, refers to the number born alive from every 100 gilts or sows, who have undergone natural mating or artificial insemination.

(3) Experimental Results

Compared with the estrus rate in the gilts in batch farrowing with FTAI, the estrus rate in the gilts in the treatment groups with different doses of 1-[bis(4-cyanophenyl)methyl]-1,2,4-triazole had no significant difference. The estrus rate in the 1-[bis(4-cyanophenyl)methyl]-1,2,4-triazole group at 20 µg/kg·BW was slightly lower than that in the 1-[bis(4-cyanophenyl)methyl]-1,2,4-triazole group at 12 µg/kg·BW. Compared with the pregnancy and farrowing rates in the gilts in the batch farrowing with FTAI, the pregnancy and farrowing rates in the gilts in the batch farrowing with FTAI in combination with low-dose 1-[bis(4-cyanophenyl)methyl]-1,2,4-triazole (treatment groups 1, 2, and 3) were both significantly increased (Table 3).

TABLE 3

Effects of compound on pregnancy and farrowing rates in gilts in batch farrowing with FTAI

| Grouping | Number of experimental animals | Estrus rate (%) | Number of mated animals | Pregnancy rate (%) | Delivery rate (%) |
|---|---|---|---|---|---|
| Precise | 62 | 93.55 | 62 | 77.42[a] | 70.97[a] |
| Treatment group 1 | 50 | 92.00 | 50 | 92.00[b] | 88.00[b] |
| Treatment group 2 | 48 | 93.75 | 48 | 95.83[b] | 83.33[b] |
| Treatment group 3 | 54 | 88.89 | 54 | 85.19[b] | 81.48[b] |

Note:
Various lowercase letters indicated significant differences in various indexes than the gilts in the batch farrowing with FTAI, $P < 0.05$.

TABLE 4

Effects of compound on farrowing by gilts in batch farrowing with FTAI

| Grouping | Total number born litter size | Healthy litter size | Stillborn + mummy | Weak litter | Live litter size | Piglet index |
|---|---|---|---|---|---|---|
| Precise | 13.24 ± 0.41 | 10.72 ± 0.39[a] | 1.96 ± 0.24 | 0.56 ± 0.15 | 11.32 ± 0.40[a] | 803 |
| Treatment group | 13.96 ± 0.30 | 12.12 ± 0.32[b] | 1.80 ± 0.22 | 0.24 ± 0.10 | 12.44 ± 0.30[b] | 1094 |
| Treatment group | 13.76 ± 0.62 | 11.72 ± 0.43[a] | 1.56 ± 0.16 | 0.28 ± 0.09 | 12.00 ± 0.45[a] | 1000 |
| Treatment group | 14.04 ± 0.53 | 11.76 ± 0.37[a] | 1.88 ± 0.39 | 0.40 ± 0.10 | 12.04 ± 0.42[a] | 981 |

Note:
Various lowercase letters indicated significant differences in various indexes than the sows in the batch farrowing with FTAI, $P < 0.05$.

were administered orally once with 1-[bis(4-cyanophenyl)methyl]-1,2,4-triazole at 20 µg/kg·BW 8 h after the injection of PMSG.

From Table 4, it could been seen that compared with the piglet index of the sows in the batch farrowing with FTAI, the piglet indexes of the sows in the batch farrowing with FTAI in combination with low-dose 1-[bis(4-cyanophenyl)methyl]-1,2,4-triazole (treatment groups 1, 2, and 3) were all significantly increased. The healthy litter size and the number born alive in the sows in treatment group 1 were both significantly higher than the healthy litter size and the number born alive in the sows in the batch farrowing with FTAI, and the healthy litter size and the number born alive in the sows in treatment groups 2 and 3 were also in an increasing trend (Table 4).

EXAMPLE 4

In this example, the effects of 1-[bis(4-cyanophenyl) methyl]-1,2,4-triazole on the estrogen level after mating and the number of ovulated oocytes in the gilts in batch farrowing with FTAI.

(1) Experimental Method and Grouping

The breed of the gilts used in this experiment was Landrace x Large White binary sows, the gilts were randomly divided into the following 3 groups, and the treatment method for each group was as follows:

batch farrowing with FTAI: the gilts were fed with an altrenogest oral solution at 20 mg/gilt at the same time every day, for 18 days; PMSG at 1000 IU/gilt was injected intramuscularly 42 h after the last feeding with altrenogest, GnRH at 100 μg/gilt was injected intramuscularly after another 80 h, the first timed insemination was performed 24 h after the injection of GnRH, and the second timed insemination was performed after 24 h.

Treatment group 1 (batch farrowing with FTAI, with supplementing with 1-[bis(4-cyanophenyl)methyl]-1,2,4-triazole (12 μg/kg·BW, orally in a single dose): The hormone treatment and mating schemes for gilts were the same as those for gilts in the batch farrowing with FTAI. The gilts were administered orally once with 1-[bis(4-cyanophenyl) methyl]-1,2,4-triazole at 12 μg/kg·BW 8 h after the injection of PMSG.

Treatment group 2 (batch farrowing with FTAI, with supplementing with 1-[bis(4-cyanophenyl)methyl]-1,2,4-triazole (20 μg/kg·BW, orally in a single dose)): The hormone treatment and mating schemes for gilts were the same as those for gilts in the precise batch farrowing with FTAI. The sows were administered orally once with 1-[bis(4-cyanophenyl)methyl]-1,2,4-triazole at 20 μg/kg·BW 8 h after the injection of PMSG.

(2) Detection of Peripheral Blood Estradiol Level in Gilts After Insemination Peripheral blood was collected from the gilts in the batch farrowing with FTAI and the batch farrowing with FTAI with supplementing with a single low dose of 1-[bis(4-cyanophenyl)methyl]-1,2,4-triazole at different times after mating, i.e., days 2, 4, 10 12, and 16 after mating, blood was collected from the anterior vena cava of the gilts and centrifuged, the supernatant was taken, stored at −20° C., and then detected for estradiol level by radioimmunoassay.

The detection steps were as follows: 12×75 mm disposable tubes were arranged on a tube rack, and were a total radioactivity counting (tc) tube, a non-specific binding (NSB) tube, a zero standard (0) tube, standard tubes, and sample tubes, respectively. 100 μL of a buffer was added to the NSB tube, 100 μL of the buffer was added to the S0 tube, 100 μL of corresponding standards were added to the standard tubes, 100 μL of corresponding samples were added to the sample tubes in order, and 100 μL of an antibody was added to all the tubes except the NSB and S0 tubes. 100 μL of 1251-E2 radioactive marker was added to all the tubes. Each tube was evenly mixed for 10 s on a spiral mixer and incubated for 2 h in a thermostat at 37° C. All the tubes were taken out, and 500 μL of ER separating agent was added to each tube. Each tube was thoroughly mixed on the spiral mixer, placed at room temperature for 20 min and centrifuged at 3500 rpm at 4° C. for 25 min, the supernatant was sucked off, and the precipitated cpm counts in each tube was measured. The binding percentages in NSB and S0 were calculated by B/T, and the binding percentages in the standards and the samples to be tested were calculated by B/BO. A standard curve was plotted on semi-logarithmic coordinate paper, and the value of a sample was found out. Alternatively, an automatic γ counter was programmed in advance to directly give the relevant parameters, standard curves and sample concentrations.

The results showed that by continuously monitoring the blood estradiol level in the gilts after mating, it was found that supplementing once with low-dose (12-20 μg/kg·BW) 1-[bis(4-cyanophenyl)methyl]-1,2,4-triazole resulted in no obvious change in the estradiol concentration in the gilts between day 2-day16 after mating (from mating to embryo implantation) (FIG. 6).

(3) Detection of Number of Ovulated Oocytes in Gilts and Expression of Key Molecules in LPA Signalling Pathway in Uterus The gilts in the batch farrowing with FTAI and the gilts in the batch farrowing with FTAI supplementing once with 1-[bis(4-cyanophenyl)methyl]-1,2,4-triazole (12 μg/kg·BW) were slaughtered. The gilts were slaughtered 16 days after mating, with 4 gilts slaughtered per group. By judging the number of corpora lutea on the ovary, the number of ovulated oocytes (each corpus luteum represented an ovulation point) was confirmed.

Figures 7A, 7B, 8:
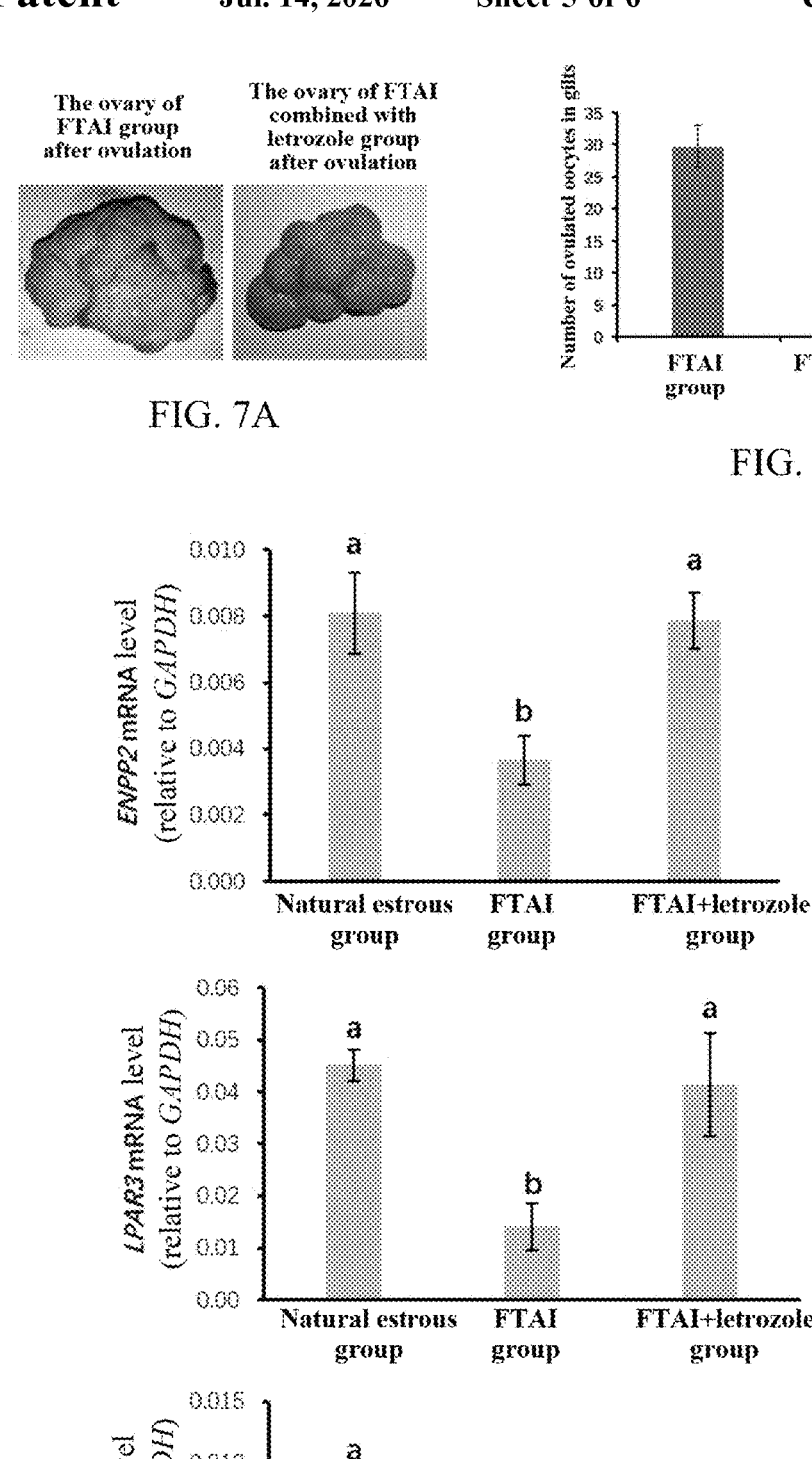
FIGS. 7A and 7B shows that the batch farrowing with FTAI in combination with a low dose of 1-[bis(4-cyanophe-nyl)methyl]-1,2,4-triazole has no significant effect on the number of ovulated oocytes in the sows. In the figure, the supplementing concentration of 1-[bis(4-cyanophenyl) methyl]-1,2,4-triazole is 12 μg/kg·BW.
FIG. 8 shows the regulation of the expression of key molecules in the LPA signalling pathway in the uterus of sows by 1-[bis(4-cyanophenyl)methyl]-1,2,4-triazole. The supplementing concentration of 1-[bis(4-cyanophenyl) methyl]-1,2,4-triazole is 12 μg/kg·BW. Different lowercase letters represent significant ($P < 0.05$).

The results showed that compared with the sows in the batch farrowing with FTAI, supplementing with a single low dose of 1-[bis(4-cyanophenyl)methyl]-1,2,4-triazole (12 μg/kg·BW) had no significant effect on the number of ovulated oocytes in the gilts (FIGS. 7A and 7B). Uteri were isolated from the gilts for RNA extraction, reverse transcription and quantitative PCR detection of several key molecules in the LPA signalling pathway, i.e., detection of ENPP2 (a gene for the expression of ATX, the key enzyme of LPA synthesis), LPAR3 (LPA receptor gene), and PTGS2 (a key gene downstream of LPAR). The control group had gilts that were in natural estrus and artificially inseminated.

The results showed that compared with the natural estrus group, the batch farrowing with FTAI group had significantly decreased Enpp2, Lpar3 and ptgs2 mRNA levels, whereas the levels in the uteri of the gilts in the batch farrowing with FTAI+1-[bis(4-cyanophenyl)methyl]-1,2,4-triazole group had no significant difference from those in the natural estrus group, but were significantly higher than those in the batch farrowing with FTAI group (FIG. 8).

It could thus be seen that in the batch farrowing with FTAI in combination with low-dose 1-[bis(4-cyanophenyl) methyl]-1,2,4-triazole, the embryo spacing was regulated with 1-[bis(4-cyanophenyl)methyl]-1,2,4-triazole by adjusting the LPA signalling pathway, thereby alleviating the overcrowding of embryos during precise batch farrowing, thus promoting the survival of embryos in gilts during pregnancy. Under the premise of not affecting the estrus rate, ovulation time, and number of ovulated oocytes in gilts, without causing decreased estrogen level, the embryo spacing upon embryo implantation in multiparous animals was increased, whereby the farrowing rate, number born alive and piglet index of livestock sows as multiparous animals were significantly improved.

INDUSTRIAL APPLICABILITY OF THE DISCLOSURE

At present, it has been difficult for the traditional continuous production mode to adapt to the rapid development of the pig farming industry. In addition, the whole live pig market is facing severe challenges. batch farrowing with FTAI technology has become an important measure for transformation and upgrading. In the future, the era of small-scale pig farming will become history, and the emerging large-scale and batch management systems will surely bring earth-shaking changes to the pig farming industry.

Figure 9:
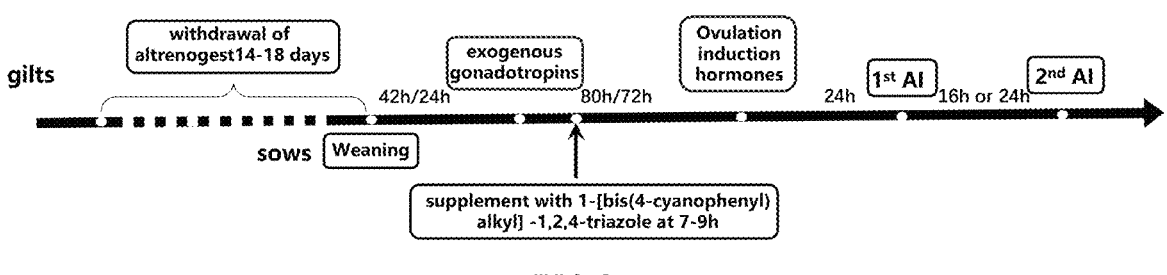
FIG. 9 shows an exemplary flow chart of batch farrowing with FTAI in combination with 1-[bis(4-cyanophenyl)al-kyl]-1,2,4-triazole.

The batch management systems technology, especially the FTAI, has also encountered some problems in the practical application process. However, from the research in the disclosure, it has been found that the method established based on 1-[bis(4-cyanophenyl)alkyl]-1,2,4-triazole for improving the effect of batch farrowing with FTAI (FIG. 9) provides important value for the popularization and application of batch farrowing with FTAI. On that basis of batch farrowing with FTAI, the disclosure further effectively improves the farrowing rate, number born alive and piglet index of gilts or sows in batch. By means of the disclosure, 190 live piglets (weaned piglets) can be increased by every 100 gilts. After calculation based on the market price of 350-450 Chinese yuan per weaned piglet, an economic value of 66,000-85,000 Chinese yuan per 100 gilts will be increased additionally by means of the disclosure, which provides an effective method for reducing costs and increasing efficiency in the whole pig farming industry. Therefore, the disclosure will create huge economic value and social value for promoting batch farrowing in swine.

Although the disclosure has been described with reference to exemplary embodiments, it should be understood that the disclosure is not limited to the disclosed exemplary embodiments. Without departing from the scope or spirit of the disclosure, various adjustments or changes can be made to the exemplary embodiments in the description of the disclosure. The scope of the claims should be based on the broadest interpretation in order to cover all modifications and equivalent structures and functions.

The invention claimed is:

1. A batch farrowing method in swine for improving the farrowing rate or the number of piglets born alive, comprising:
 (1) administering exogenous gonadotropin(s) at a dosage of 100-10, 000 IU/animal to a batch of female pigs with estrus synchronization to synchronize follicular development;
 (2) administering 1-[bis(4-cyanophenyl) methyl]-1,2,4-triazole only to the batch of female pigs with synchro-nized follicular development at 6-11.5 hours after finishing step (1) to regulate embryo spacing in a pig during pregnancy, so as to obtain a batch of treated female pigs; and
 (3) administering ovulation induction drug(s) to the batch of treated female pigs and performing fixed-time artificial insemination;
 wherein the 1-[bis(4-cyanophenyl) methyl]-1,2,4-triazole is fed once or twice to a total dosage of 10-50 μg/kg.BW, and the exogenous gonadotropin(s) is only administered in step (1).

2. The batch farrowing method for improving the farrowing rate or the number of piglets born alive in female pigs according to claim 1, wherein prior to step (1), a batch of gilts are administered with a progestogen, or a batch of sows are weaned synchronously to synchronize estrus.

3. The batch farrowing method for improving the farrowing rate of or the number of piglets born alive of female pigs according to claim 2, wherein the progestogen is altrenogest administered at a dosage of 10-30 mg/gilt/day for 10-20 days.

4. The batch farrowing method for improving the farrowing rate or the number of piglets born alive in female pigs according to claim 1, wherein a mating time begins at 15-60 hours after ovulation induction drug is administered.

5. The batch farrowing method for improving the farrowing rate or the number of piglets born alive in female pigs according to claim 1, wherein a fixed-time artificial insemination is carried out multiple times, the first insemination is at 15-26 hours after ovulation induction drug is administered, and the second insemination is at 10-30 hours after the first insemination.

6. The batch farrowing method for improving the farrowing rate or the number of piglets born alive in female pigs according to claim 1, wherein the exogenous gonadotropins comprise at least one exogenous gonadotropin selected from the group consisting of follicle-stimulating hormone, luteinizing hormone, and pregnant mare serum gonadotropin; and
 wherein the ovulation induction drug comprises at least one ovulation inducing drug selected from the group consisting of gonadorelin, buserelin, recombinant porcine luteinizing hormone, clomiphene, chorionic gonadotropin, postmenopausal gonadotropin, gonadotrophin releasing hormone, and a gonadotrophin releasing hormone agonist.

7. The batch farrowing method for improving the farrowing rate or the number of piglets born alive in female pigs according to claim 1, wherein the 1-[bis(4-cyanophenyl) methyl]-1,2,4-triazole is administered orally.

* * * * *